United States Patent
Zeng et al.

(10) Patent No.: US 9,809,622 B2
(45) Date of Patent: Nov. 7, 2017

(54) TUMOR-TARGETING POLYPEPTIDE AND APPLICATION THEREOF

(71) Applicant: Sun Yat-sen University Cancer Center, Guangzhou (CN)

(72) Inventors: Musheng Zeng, Guangzhou (CN); Xing Zhang, Guangzhou (CN); Jun Wang, Guangzhou (CN); Guokai Feng, Guangzhou (CN); Mengqing Zhang, Guangzhou (CN); Qian Zhong, Guangzhou (CN)

(73) Assignee: Sun Yat-Sen University Cancer Center, Guangdong (CN)

( * ) Notice: Subject to any disclaimer, the term of this patent is extended or adjusted under 35 U.S.C. 154(b) by 0 days.

(21) Appl. No.: 15/021,366

(22) PCT Filed: Sep. 5, 2014

(86) PCT No.: PCT/CN2014/085954
§ 371 (c)(1),
(2) Date: Jul. 27, 2016

(87) PCT Pub. No.: WO2015/035881
PCT Pub. Date: Mar. 19, 2015

(65) Prior Publication Data
US 2016/0355548 A1    Dec. 8, 2016

(30) Foreign Application Priority Data

Sep. 11, 2013 (CN) .......................... 2013 1 0413634

(51) Int. Cl.
| | | |
|---|---|---|
| *A61K 38/00* | (2006.01) |
| *A61K 38/03* | (2006.01) |
| *A61K 38/08* | (2006.01) |
| *A61K 38/10* | (2006.01) |
| *A61K 51/08* | (2006.01) |
| *C07K 7/06* | (2006.01) |
| *C07K 7/08* | (2006.01) |
| *C07K 7/00* | (2006.01) |
| *A61K 47/48* | (2006.01) |
| *A61K 49/00* | (2006.01) |

(52) U.S. Cl.
CPC .......... *C07K 7/06* (2013.01); *A61K 47/48246* (2013.01); *A61K 49/0056* (2013.01); *A61K 51/08* (2013.01); *A61K 51/088* (2013.01); *C07K 7/08* (2013.01); *A61K 38/00* (2013.01)

(58) Field of Classification Search
CPC ........ A61K 38/00; A61K 38/03; A61K 38/08; A61K 38/10; A61K 47/48246; A61K 49/0056; A61K 51/08; A61K 51/088; C07K 7/06; C07K 7/08; C07K 7/00
USPC .... 514/19.2, 21.5, 21.6, 21.7; 530/327, 328, 530/329
See application file for complete search history.

(56) References Cited

U.S. PATENT DOCUMENTS

| | | | | |
|---|---|---|---|---|
| 2004/0181830 | A1* | 9/2004 | Kovalic | C07K 14/415 800/289 |
| 2013/0333061 | A1* | 12/2013 | Wu | C07K 14/415 800/260 |

FOREIGN PATENT DOCUMENTS

| | | |
|---|---|---|
| CN | 102432671 | 5/2012 |
| CN | 103254280 | 8/2013 |
| WO | 2007087370 | 8/2007 |
| WO | 2008100481 | 8/2008 |
| WO | 2009155556 | 12/2009 |
| WO | 2013049830 | 4/2013 |

* cited by examiner

*Primary Examiner* — Julie Ha
(74) *Attorney, Agent, or Firm* — Lowenstein Sandler LLP

(57) ABSTRACT

A tumor-targeting peptide is disclosed. This tumor-targeting peptide comprises a typical motif with the general formula of: XX(Y/F) (D/E) (D/E) XX. The motif is selectively connected with 1-3 amino acids at the C-terminal and/or N-erminal. X represents any one of the twenty natural amino acids or the D type amino acids. The present invention also discloses that the peptide can not only target tumor vessels and tumor cells but also penetrate them and thus can be applied in tumor diagnosis and therapy.

8 Claims, 7 Drawing Sheets

1A

1B

1C

2A

2B

2C

5B

Tumor

5A

Tumor

7A

7B

7C

7D

7E

7F

SEQUENCE LISTING

```
<160> NUMBER OF SEQ ID NOS: 8

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide sequence
<220> FEATURE:
<221> NAME/KEY: DISULFID
<222> LOCATION: (1)..(9)

<400> SEQUENCE: 1

Cys Arg Trp Tyr Asp Glu Asn Ala Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide sequence
<220> FEATURE:
<221> NAME/KEY: DISULFID
<222> LOCATION: (1)..(9)

<400> SEQUENCE: 2

Cys Gly Gly Gly Gly Gly Gly Gly Cys
1               5

<210> SEQ ID NO 3
<211> LENGTH: 25
<212> TYPE: PRT
<213> ORGANISM: Artificial Sequence
<220> FEATURE:
<223> OTHER INFORMATION: Synthetic peptide sequence
<220> FEATURE:
<221> NAME/KEY: DISULFID
<222> LOCATION: (17)..(25)

<400> SEQUENCE: 3

Lys Leu Ala Lys Leu Ala Lys Lys Leu Ala Lys Leu Ala Lys Gly Gly
1               5                   10                  15

Cys Arg Trp Tyr Asp Glu Asn Ala Cys
            20                  25

<210> SEQ ID NO 4
<211> LENGTH: 25
<212> TYPE: PRT
<213> ORGANISM: Artifical Sequence
<220> FEATURE:
<223> OTHER INFORMATION: Synthetic peptide sequence
<220> FEATURE:
<221> NAME/KEY: DISULFID
```

```
<222> LOCATION: (17)..(25)

<400> SEQUENCE: 4

Lys Leu Ala Lys Leu Ala Lys Lys Leu Ala Lys Leu Ala Lys Gly Gly
1               5                   10                  15

Cys Arg Trp Tyr Asp Glu Asn Ala Cys
            20                  25

<210> SEQ ID NO 5
<211> LENGTH: 25
<212> TYPE: PRT
<213> ORGANISM: Artificial Sequence
<220> FEATURE:
<223> OTHER INFORMATION: Synthetic peptide sequence
<220> FEATURE:
<221> NAME/KEY: DISULFID
<222> LOCATION: (17)..(25)

<400> SEQUENCE: 5

Lys Leu Ala Lys Leu Ala Lys Lys Leu Ala Lys Leu Ala Lys Gly Gly
1               5                   10                  15

Cys Gly Gly Gly Gly Gly Gly Gly Cys
            20                  25

<210> SEQ ID NO 6
<211> LENGTH: 14
<212> TYPE: PRT
<213> ORGANISM: Artificial Sequence
<220> FEATURE:
<223> OTHER INFORMATION: Synthetic peptide sequence

<400> SEQUENCE: 6

Lys Leu Ala Lys Leu Ala Lys Lys Leu Ala Lys Leu Ala Lys
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(2)
     (223) Xaa can be any naturally occurring amino acid
<220> FEATURE:
<221> NAME/KEY: CONFLICT
<222> LOCATION: (3)..(3)
<223> OTHER INFORMATION: Tyr can be replaced by Phe
<220> FEATURE:
<221> NAME/KEY: CONFLICT
<222> LOCATION: (4)..(5)
<223> OTHER INFORMATION: Asp can be replace by Glu
<220> FEATURE:
<221> NAME/KEY: misc_feature
<222> LOCATION: (6)..(7)
<223> OTHER INFORMATION: Xaa can be any naturally occurring amino acid

<400> SEQUENCE: 7

Xaa Xaa Tyr Asp Glu Xaa Xaa
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide sequence
<220> FEATURE:
```

```
<221> NAME/KEY: DISULFID
<222> LOCATION: (1)..(7)

<400> SEQUENCE: 8

Arg Trp Tyr Asp Glu Asn Ala
1               5
```

TUMOR-TARGETING POLYPEPTIDE AND APPLICATION THEREOF

CROSS-REFERENCE TO RELATED APPLICATIONS

This application is a National Phase U.S. Patent Application claiming priority of International Application No. PCT/CN2014/085954, filed Sep. 5, 2014 which claims priority of Chinese Patent Application No. 201310413634.5, filed on Sep. 11, 2013, the disclosures of which are hereby incorporated by reference herein in their entirety.

FIELD OF THE INVENTION

The present invention relates to a targeting peptide, particularly a tumor-targeting peptide, and its application.

BACKGROUND OF THE INVENTION

Peptides that become prevalent in tumor vessels or tumor cells by specifically binding to surface molecules of tumors are usually used as tumor targeting reagents.

Tumor-targeting peptides have an important value when applied to diagnosis of tumor and targeted treatment. On the one hand, tumor-targeting peptides coupled with imaging molecules could be applied to tumor imaging; on the other hand, tumor-targeting peptides coupled with anti-tumor drugs could be used in tumor-targeted treatment. For example, Professor Errki, an academician of the National Academy of Science, reported a tumor-targeting peptide containing RGD motif, which binds to integrin αv of angiogenic blood vessels in tumor. Based on Professor Errki's study, many tumor-targeting peptides containing this RGD motif have emerged in the clinical research and some of the peptides have gotten satisfactory results. One of the tumor-targeting peptide containing RGD motif is called "Cliengtide." "Cliengtide" has shown good efficacy on glioma during Phase II clinical trial and has entered Phase III clinical trial stage.

Based on the targeting and penetrating features of tumor-targeting peptides, Professor Errki divided them into 4 types: the first type can target tumor vessels; the second type can target tumor cells; the third type can target both tumor vessels and tumor cells; the fourth can target and penetrate both tumor vessels and tumor cells by binding to tumor vessels and tumor cells, and entering the tumor's cytoplasm through tumor cell membrane. Professor Errki considered the fourth type such as the iRGD peptide as the most ideal tumor-targeting peptides.

SUMMARY OF THE INVENTION

The aim of the present invention is to provide a tumor-targeting peptide and its application.

The technical solutions of the present invention are as follows:

A tumor-targeting peptide with typical motif: XX(Y/F)(D/E)(D/E)XX (SEQ ID No:7). The motif may optionally be connected with 1-3 amino acids at the C-terminal and/or N-terminal. X represents any one of the twenty natural amino acids or the D type amino acids thereof.

In one preferred embodiment, the motif of the peptide is XXYDEXX.

In one preferred embodiment, the peptide may be cyclized by the terminal amino acids in two ends.

In one preferred embodiment, each of the two ends of the peptide may be connected with one Cys, respectively.

In one preferred embodiment, the sequence motif of the peptide is RWYDENA (SEQ ID NO:8)

A tumor-targeting reagent containing any one of the peptides described above.

The beneficial effects of the present invention:

The tumor-targeting peptide can target and penetrate tumor vessels and tumor cells, which can be an ideal tumor-targeting peptide with important value in diagnostic applications of tumor molecules and tumor-targeted treatment.

The invented peptide coupled with a molecular marker can bind to tumor cells and be used in tumor screening and diagnosis.

The invented peptide coupled with drugs can be used for tumor-targeted treatments.

DETAILED DESCRIPTION OF THE EMBODIMENTS

Figure 1A:
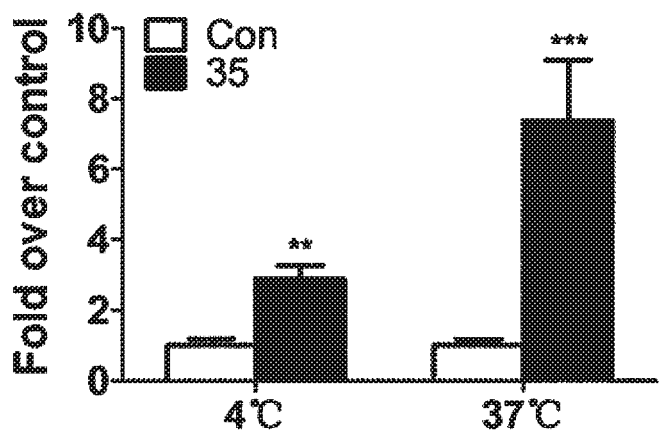
FIGS. 1A-1C show results of tumor-targeting experiments.

A tumor-targeting peptide with typical motif: XX(Y/F)(D/E)(D/E)XX. The motif may optionally be connected with 1-3 amino acids at the C-terminal and/or N-terminal. X represents any one of the twenty natural amino acids or the D type amino acids thereof.

In one preferred embodiment, the motif of the peptide is XXYDEXX.

In one preferred embodiment, the sequence motif of the peptide is RWYDENA.

In one preferred embodiment, the peptide may be cyclized by the terminal amino acids in two ends.

The resulting cyclic peptide may be more stable and may have a longer efficacy in vivo.

In one preferred embodiment, two ends of the peptide may be connected with one Cys, respectively.

More preferably, the peptide may be cyclized via a disulfide bond formed by the two Cysteines at the two ends.

The present invention also involves a tumor-targeting reagent coupled with any one of the above tumor-targeting peptides, in which the peptide is responsible for tumor targeting. The effective molecule coupled with the peptide may be a diagnostic reagent(s) or a drug(s), such as a tumor-killer peptide, or a small molecule chemotherapeutic drug. To ensure an improved connection between the effective molecule and peptides, coupling groups commonly used in the art may be applied. To ensure the effective targeting, the binding site should not be contained in the typical motif.

The tumor-targeting peptides described above can be formed by levorotatory (L) amino acids or dextro (D) amino acids. The dextro (D) amino acids are ideal choices because they can exist more stably in vivo.

The peptides used in the experiments are as follows:

| The name of peptide | Sequence (italic representing cyclization of 2 Carbons) | SEQ ID NO: |
|---|---|---|
| 35 | *CRWYDENAC* | 1 |
| Con | *CGGGGGGGC* | 2 |
| Biotin-35 | Biotin-*CRWYDENAC* | |
| Biotin-C | Biotin-*CGGGGGGGC* | |
| Cy5-35 | Cy5-*CRWYDENAC* | |
| Cy5-C | Cy5-*CGGGGGGGC* | |
| 35-AP | D (KLAKLAKKLAKLAK)-GG-*CRWYDENAC* | 3 |
| (35-AP)D | D (*KLAKLAKKLAKLAK-GG-CRWYDENAC*) | 4 |
| C-AP | D (KLAKLAKKLAKLAK)-GG-*CGGGGGGGC* | 5 |
| AP | D (KLAKLAKKLAKLAK) | 6 |
| HYNIC-35 | HYNIC-*CRWYDENAC* | |
| HYNIC-C | HYNIC-*CGGGGGGGC* | |

Analysis of Data

The results of counting were analyzed by SPSS16.0. Homogeneity of variance was calculated by Levene Variance Equality Test. If P>0.05, independent-samples t test will be applied to examine statistically significant differences among groups.

Tumor Targeting Experiments:

Based on the cell-binding counts of phage T7 expressing 35-peptide, the ability of the 35-peptide targeting cells was indirectly reflected. So, the first step was to construct phage T7 exogenously expressing 35-peptide, then calculate the cell-binding counts of the phages, which indicates the binding ability of the 35-peptide to cells. The details will be described hereinafter.

1) Synthesizing DNA coding containing the targeting peptide with phosphorylation in the 3' end, and annealing under the condition shown in the following table:
2)

| Number | Reaction System | Volume (μl) |
|---|---|---|
| 1 | dH$_2$O | 7 |
| 2 | 10× reaction Buffer | 3 |
| 3 | 10 μM DNA coding sense strand (3' phosphorylation) | 20 |
| 4 | 10 μM DNA coding anti-sense strand (3' phosphorylation) | 20 |

3) Heating the reaction to 95° C. and holding for 5 min, then positioning the products on ice for cooling.
4) Performing the agarose gel electrophoresis on the reaction products from step 2) with 4% TBE (Tris-borate-Ethylenediaminetetraacetic acid); identifying the products before and after annealing (the products before annealing are single strand DNA and the products after annealing are double strand DNA and thus the annealed products run slower than products before annealing during the process of gel electrophoresis).
5) Inserting the DNA coding containing the targeting peptide into phageT7 under the following condition:

| Number | Reaction System | Volume (μl) |
|---|---|---|
| 1 | Annealed products | 1 |
| 2 | T7 select vector arms | 1 |
| 3 | Ligation high | 2 |

6) Ligating for two hours at 16° C.
7) Thawing the T7 select packaging extract on ice, then adding the ligation products, and packing at 22° C. for two hours.
8) Adding 270 μl LB (Ligase Buffer) to stop the reaction, and the ligation products were diluted 10-fold by serial dilution, then spreading these serial dilutions on plates to count the number of T7 phages.

The phage counting assay was conducted to first test the binding ability of phage 35 to nasopharyngeal carcinoma cell line, CNE2 and then test whether the 35 peptide can block the binding of the phage 35 to CNE2. The process will be described in detail hereinafter.

1) Trypsinizing cells, counting to obtain $1.0*10^6$ cells/tube, and re-suspending cells with 200 μl RPMI (Roswell Park Memorial Institute) 1640 medium;
2) For the blocking test, adding the 35 peptide at a corresponding concentration and incubating on ice for 30 minutes (the binding assay skips this step and directly goes to the third step);
3) Adding $1.0*10^8$ phages, and incubating on ice for binding for one hour;
4) After washing with 1 ml PBS (Phosphate Buffered Saline), the resulting products were centrifuged at 400 g force for 5 min; repeating this step three times;
5) Re-suspending the precipitate with 1 ml TBS (Tris Buffered Saline), diluting the resulting suspension liquid $10^3$-$10^4$ fold, and only taking 100 μl for phage count assay;
6) Inoculating BL21 competent cell for T7 phage with 1:100 v/v, then shaking at 200 RPM at 37° C. for four hours until OD600 (Optical Density at a wavelength of 600 nm) reaches 0.5-1.0 when the bacteria are on the logarithmic phase. The bacteria was stored for use at 4° C. for 24 hours;
7) Preheating the bottom agar at 37° C. and preheating the upper agar at 45° C. in water bath;
8) Diluting phages with a 10-fold serial dilution in gradient of LB, a new pipette tip was used during a new dilution process and diluted phages with different concentrations were prepared in separate eppendorf tubes;
9) Adding 100 μl BL21 in the logarithmic phase of growth and 100 μl diluted phages to be identified into a 4 ml tube;
10) Adding 4 ml preheated upper agar (45° C.) to the tube, and immediately pouring this upper agar onto the plate with the preheated bottom agar (37° C.), then solidifying at room temperature for 5 min
11) Incubating the plate at 37° C. for 4 hours, counting the plaque on the plate. The titer of phage was calculated based on the diluted factors.

Flow cytometry analysis was applied to detect the binding affinity of Cy5-35 peptide to nasopharyngeal carcinoma cell CNE2. Firstly, the 35 peptide and control peptides separately coupled with fluorescent dye Cy5 were synthesized. Then, Cy5-35 peptide were incubated with cells. At the end, the binding efficacy was calculated using the flow cytometry analysis. Detailed steps were as followed:
1) Trypsinizing cells, counting and adjusting the concentration to $1.0*10^6$ cells/tube, and re-suspending cells with 200 µl RPMI 1640 medium;
2) Adding Cy5-Control peptide or Cy5-35 peptide dissolved with PBS at a concentration of 5 µM or 10 µM, then incubating on ice for 30 minutes.
3) Washing with 1 ml PBS, then centrifuging at 400 g force for 5 minutes; repeating this step twice;
4) Re-suspending the precipitate with 1 ml TBS,
5) Conducting the flow cytometry analysis.

Figure 1B:
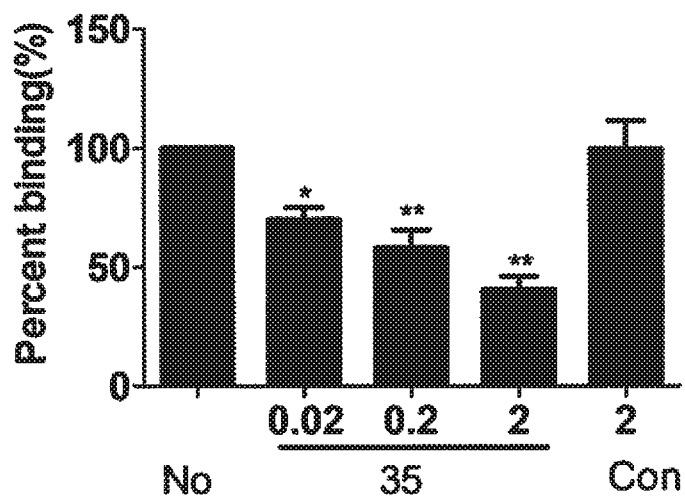
Figure 1C:
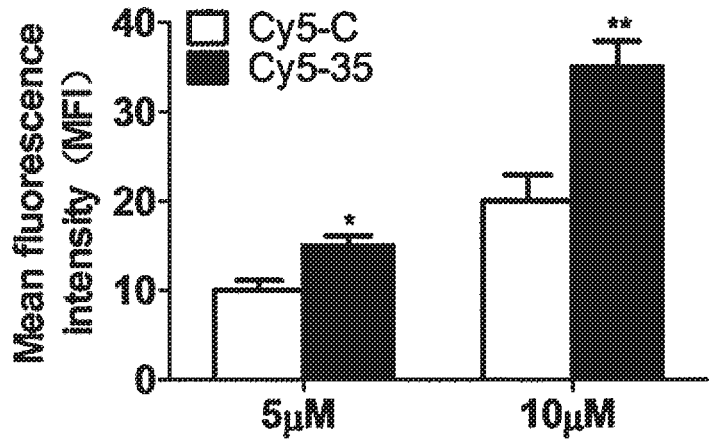

As shown by phage counting assays at 4° C. or 37° C. in FIG. 1, the phage 35 shows strong binding ability with nasopharyngeal carcinoma cell CNE2, compared to the control (FIG. 1A). 35 peptide prevents phage 35 from binding to CNE2 in a dose-dependent manner in the blocking assay (FIG. 1B). Cy5-35 peptide binds to CNE2 cells in a dose-dependent manner using the flow cytometry analysis (FIG. 1C). According to these results, 35 peptide has the specific-targeting potential to nasopharyngeal carcinoma cells.

Assay for Penetrating Cancer Cells:

The phage counting assay was applied to test whether 35 phage can penetrate the cell membrane and enter the nasopharyngeal carcinoma cell CNE2. Most steps were the same as the tumor targeting experiments except steps 2)-4) were replaced as followed:
2) Adding $1.0*10^8$ T7 phages expressing 35 peptide or control peptide, incubating at 37° C. for one hours;
3) Washing with 1 ml PBS, then centrifuging at 400 g force for 5 minutes; followed by washing with 1 ml 0.1M Glycinate hydrochloride and 500 mM sodium chloride, then centrifuging at 400 g force for 5 minutes; then washing again with 1 ml PBS, then centrifuging at 400 g force for 5 minutes;
4) Re-suspending the precipitate with 1 ml 1% NP-40 TBS, diluting $10^3$-$10^4$ fold, and then taking 100 ul for phage counting assay.

The flow cytometry analysis was applied to detect whether phage 35 can penetrate the nasopharyngeal carcinoma cells CNE2. Detailed steps were as followed:
1) Incubating Cy5-35 peptide or Cy5-control peptide with cells at 37° C. for two hours;
2) Trypsinizing cells, counting and adjusting the concentration to $1.0*10^6$ cells/tube, and re-suspending cells with 200 µl RPMI 1640 medium;
3) Washing with 1 ml PBS, then centrifuging at 400 g force for 5 minutes, repeating it three times;
4) Re-suspending the precipitate with 1 ml PBS;
5) Conducting the flow cytometry analysis.

The cellular immunofluorescence assay was applied to detect whether Biotin-35 peptide can penetrate CNE2 cells. Detailed steps were as followed:
1) Incubating Biotin-35 peptide or Biotin-control peptide with cells at 37° C. for two hours;
2) Washing three times with 1 ml PBS for 5 minutes;
3) Fixing the cells with 4% paraformaldehyde for 10 minutes;
4) Incubating cells with 0.1% Triton-X100 for 5 minutes;
5) Blocking with 5% BSA for 30 minutes;
6) Washing with 1 ml PBS twice;
7) Adding FITC-streptavidin and avoiding light for one hour;
8) Washing three times with 1 ml PBS for 5 minutes;
9) Adding DAPI at a ratio of 1:2000 and keeping it away from light at room temperature for 5 minutes,
10) Washing with 1 ml PBS for 5 minutes,
11) Mounting samples with Anti-fade, and observing the samples under the laser confocal microscope.

Figure 2A:
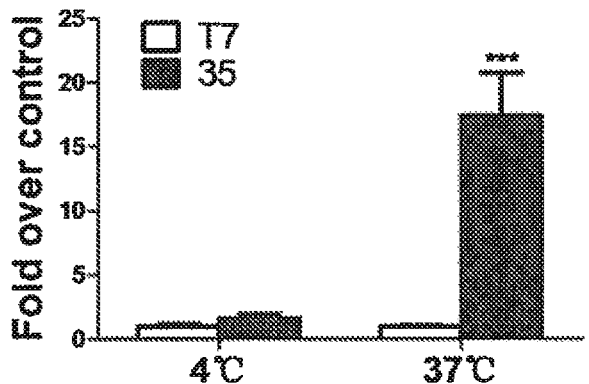
FIGS. 2A-2C show results of tumor-penetrating experiments.
Figure 2B:
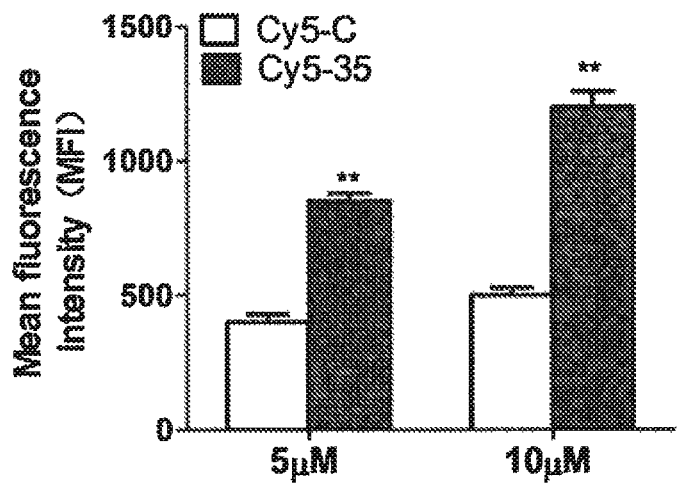
Figure 2C:
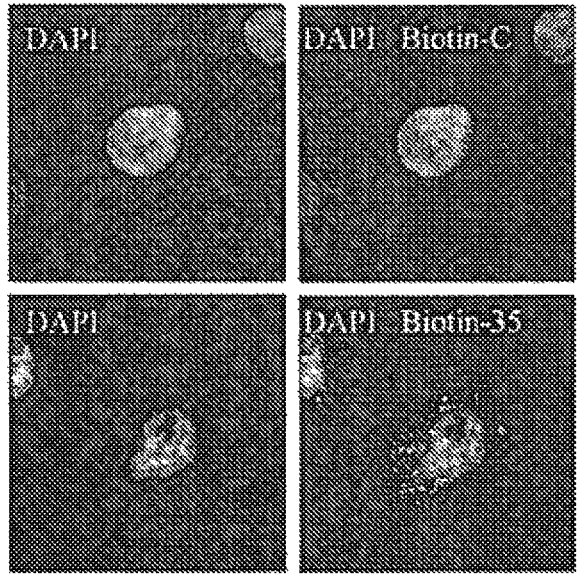

As shown in FIG. 2, few of phage 35 penetrated CNE2 at 4° C. However, the penetration level was significantly enhanced at 37° C. (FIG. 2A). Cy5-35 peptide penetrates into CNE2 in a dose-dependent manner in flow cytometry analysis (FIG. 2B). Cellular immunofluorescence assay indicated Biotin-35 peptide is able to penetrate into CNE2 According to these results, 35 peptide can penetrate nasopharyngeal carcinoma cells.

Figures 3A, 3B:
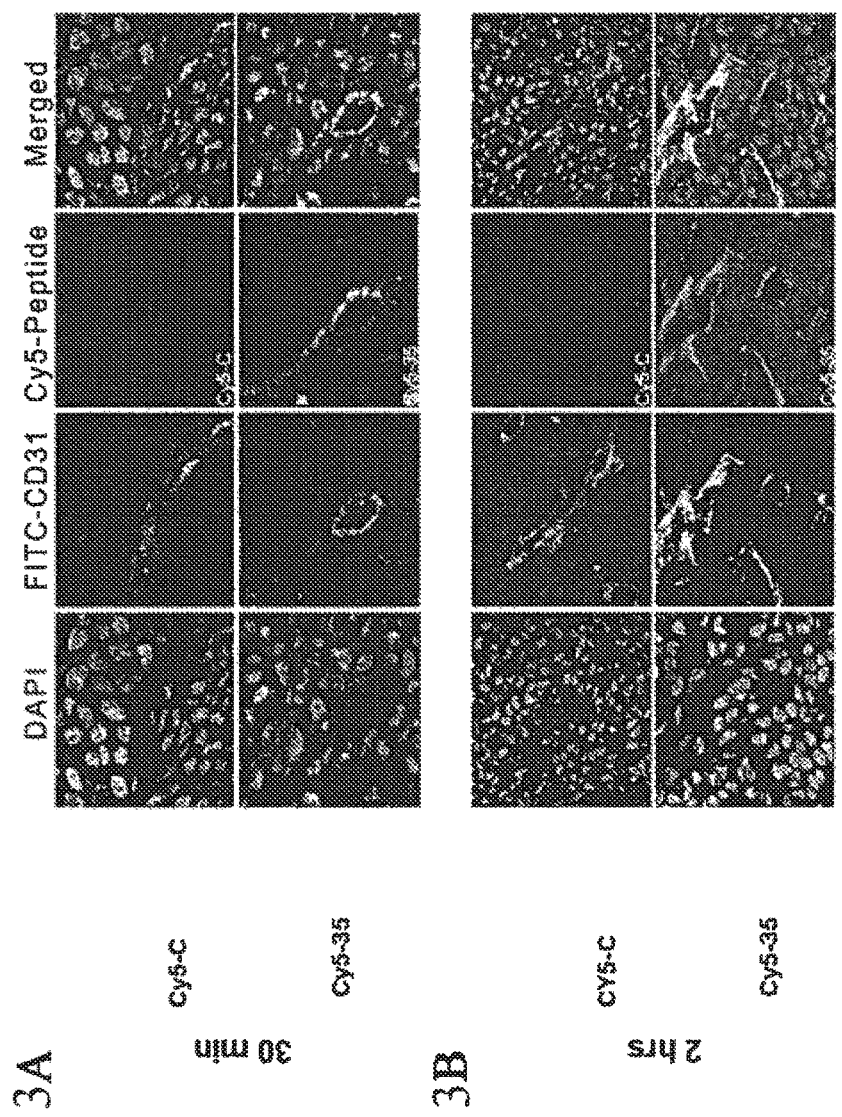
FIGS. 3A-3B show results of targeting and penetrating tumor vessels experiments.

Assay for Targeting and Penetrating Tumor Vessels and Tumor Cells:

Cy5-35 peptide is tested to target and penetrate the vessels using the frozen section and immunohistochemical assay. Detailed steps were as followed:
1) Using nine 4-week-old BALB/C nude mice
2) Trypsinizing cells, counting and adjusting the concentration to $1.0*10^6$ cells/ml, and re-suspending cells with 200 µl RPMI 1640 medium containing 20% Matrigel, then subcutaneously injecting into the nude mice;
3) Observing and measuring the size of tumor after 1-2 weeks. Based on the tumor size, the mice were randomly divided into three groups (PBS, Cy5-Control and Cy5-35, three mice in each group);
4) Intravenously injecting 200 µl PBS or 300 µg fluorescence peptide dissolved in 200 µl PBS;
5) Obtaining the tumor tissues, and making frozen sections and cutting slides, storing at −80° C.;
6) Fixing the slides in cooled acetone for 10 min, washing 5 times with PBS for 5 minutes;
7) Soaking the slides with 3% $H_2O_2$ to remove endogenous peroxidase and then washing 3 times with 1 ml PBS for 5 minutes;
8) Blocking with 10% BSA for 20 minutes at room temperature;
9) Incubating with anti-CD31 mouse first antibody at 4° C. overnight;
10) Washing 3 times with PBS for 5 minutes;
11) Incubating anti-mouse FITC second antibody at room temperature for one hour, keeping it away from light, and then washing 3 times with 1 ml PBS for 5 min;
12) Adding DAPI at room temperature and keeping for 5 minutes and then washing 3 times with 1 ml PBS for 5 minutes;
13) Covering the slides with anti-fade, then observing the slides under the laser confocal microscope As shown in FIG. 3: Half an hour after intravenously injecting Cy5-35 peptide, Cy5-35 peptide co-localized with vessel marker CD31 (FIG. 3A). After intravenously injecting Cy5-35 peptides for 2 h, Cy5-35 peptides co-localized with vessel marker CD31, and part of Cy5-35 peptides penetrated the tumor vessels and tumor cells (FIG. 3B). According to these results, the 35 peptides can target and penetrate the tumor vessels and tumor cells.

Near-Infrared Fluorescence Imaging of Tumor:

Cy5-35 peptide distribution was examined in the different organs and tumors of nude mice. Small animal imaging assay was operated as followed:
1) Using 4-week-old BALB/C nude mice;
2) Trypsinizing cells, counting and adjusting the concentration to $1.0*10^6$ cells/ml, and re-suspending cells with 200 µl RPMI 1640 medium containing 20% Matrigel, then subcutaneously injecting into the nude mice;

3) Observing and measuring the size of tumor after 1-2 weeks. Based on the tumor size, the mice were randomly divided into three groups (PBS, Cy5-Control and Cy5-35, 3 mice in each group);
4) Intravenously injecting 200 µl PBS or 300 µg fluorescence peptide dissolved in 200 µl PBS; the peptide distribution is detected in both normal organs and tumor using Caliper IVIS Lumina II;
5) Obtaining normal organs and the tumor tissues, homogenizing them, and calculating the fluorescence intensity of normal organs and the tumor for statistical analysis.

To detect whether Cy5-35 peptide can apply to other tumors, the peptides were applied to MDA-MB-231 nude mice model.

Figures 4A, 4B, 4C, 4D:
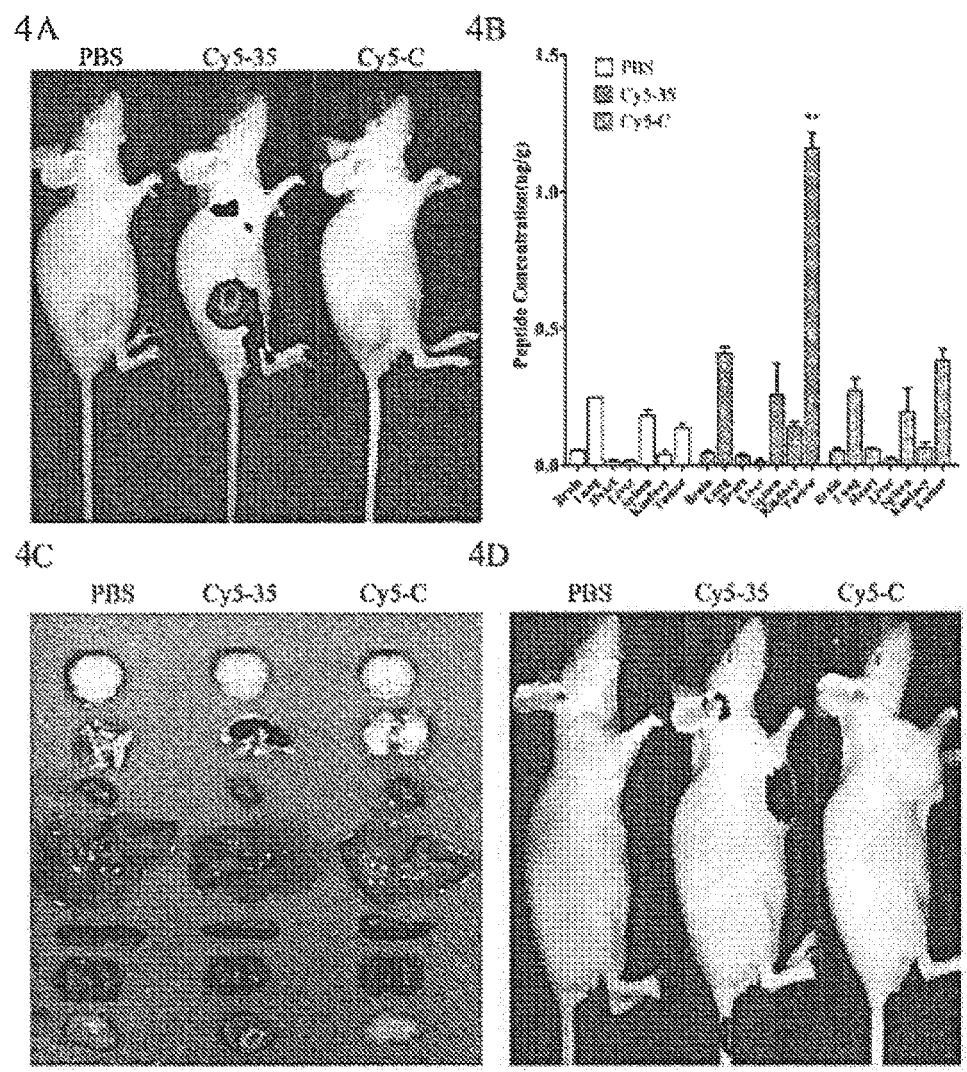
FIG. 4A-4D show results of NIR molecular imaging.

As shown in FIG. 4, after intravenous injection of fluorescence peptide for 24 hours, Cy5-35 peptide was significantly enriched in tumor (FIG. 4A), while there are certain residual peptides in lung (FIG. 4B). The intensity of fluorescence in tumor is significantly stronger than that in other organs (FIG. 4C). Moreover, Cy5-35 peptide can also be applied in breast cancer imaging (FIG. 4D). In conclusion, 35 peptide can be applied to nasopharyngeal carcinoma and breast cancer molecular imaging.

SPECT Molecular Imaging of Tumor:

The method of apply HYNIC-modified 35 peptide coupled with $^{99m}$Tc in mice for SPECT imaging is described in detail as follows:
1) Dissolving 100 µg HYNIC-35 peptide in 100 µl EDDA/tricine solution (20 mg/ml tricine, 10 mg/ml EDDA, pH 7.0);
2) Adding 20 µl tin(II) solution (dissolving 10 mg $SnCl_2.2H_2O$ in 10 ml 0.1 N HCl);
3) Adding 1 ml $^{99m}$TcO4 (800 MBq) solution;
4) Heating them to 100° C. for 10 min and then cooling them down to room temperature;
5) Intravenously injecting 100 µl fluorescence peptide to each nude mice;
6) Detecting the distribution of HYNIC-35 peptide at 2 hours, 4 hours, 6 hours, and 12 hours after injection.

Figure 5A:
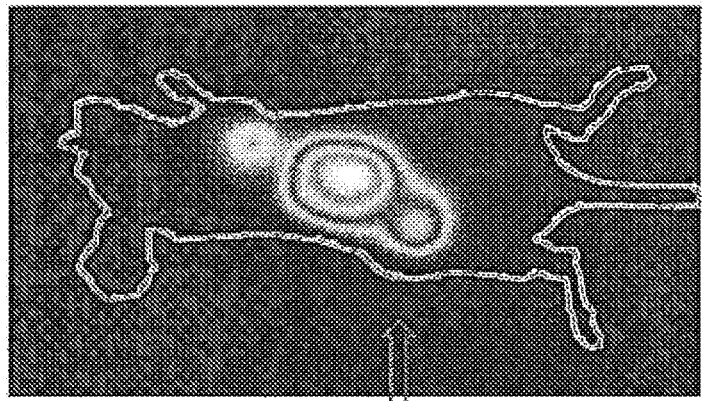
FIGS. 5A-5B show results of SPECT molecular imaging.
Figure 5B:
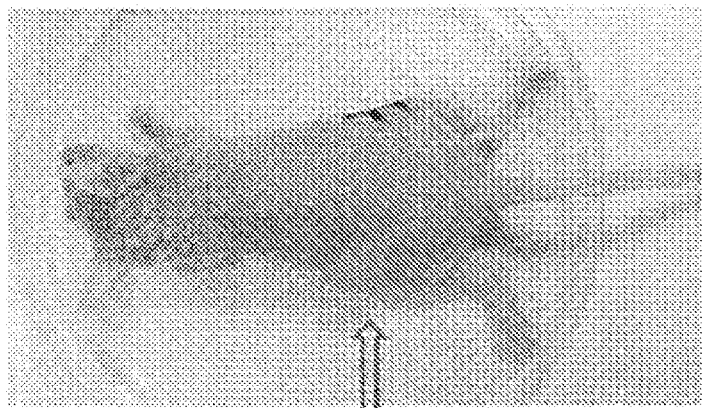

The result of SPECT shows HYNIC-35 peptide was enriched in tumor and kidney at 4 hours after injection (FIGS. 5A and 5B). All results demonstrated HYNIC-35 peptide is applicable for tumor SPECT imaging.

Targeted Treatment when Coupled with Anti-Tumor Apoptotic Peptide 35 peptide and control C were separately coupled with apoptotic peptide (AP) to form 35-AP and C-AP peptide to detect the treatment efficacy. The apoptotic peptides activate the intrinsic apoptotic pathways by breaking mitochondrial membrane to achieve the apoptosis-promoting effect. The apoptotic peptides take effect only when the peptides come into cells. The 35-AP peptide was first internalized into tumor cells and then apoptotic peptides activated the apoptotic pathways to achieve a therapeutic effect.

Therapeutic effects of 35-AP peptide were assessed by Cleaved Caspase 3/7 kit. Detailed steps were as followed:
1) After the cells were planked for 24 hours, the peptide dissolved by 1640 was incubated with cells at 37° C. for four hours;
2) Trypsinizing cells with TrypLE Expression, counting and adjusting the concentration to 1.0*10$^6$ cells/ml, and transferring 300 µl into flow cytometry tube;
3) Adding 10 µl 30*FLICA working solution;
4) Incubating the cells at 37° C. with 5% CO2 for one hour, and mixing once every 15 minutes;
5) Washing with 2 ml Washing buffer, then centrifuging at 400 g force for 5 minutes;
6) Re-suspending the precipitate with 1 ml Washing buffer;
7) Detecting the staining signal using flow cytometer.

CCK-8 kit was used to test IC50 of 35-AP peptide in different nasopharyngeal carcinoma cell lines by. Detailed steps were as followed:
1) Preparing 100 µl re-suspended cells in 96-well culture plate;
2) Adding 10 µl peptides or AP-peptides with different concentrations into the plate;
3) Incubating the plate in an incubator for 48 h;
4) Adding 10 µl CCK8 in each well;
5) Incubating the plate in an incubator for 1-4 hours;
6) Measuring absorbance at 450 nm using ELISA, then calculating IC50.

Injecting 35-AP peptide to tumor-bearing mice to detect its therapeutic effect. Detailed steps were as follows:
1) Selecting twenty four 4-week-old BALB/C nude mice;
2) Trypsinizing CNE2 cells, counting and adjusting the concentration to 1.0*10$^6$ cells/ml, and re-suspending cells with 200 µl RPMI 1640 medium containing 20% Matrigel, then subcutaneously injecting 200 µl re-suspended cells into the nude mice;
3) Observing and measuring the size of tumor after 1-2 weeks. Based on the tumor size, the mice were randomly divided into three groups (PBS, Control AP and 35-AP);
4) Intravenously injecting 200 µl PBS or 200 µg fluorescence peptide dissolved in 200 µl PBS every other day for 6 times in total. Measuring the length and width of tumor before and after injection. The volume of tumor=0.52* (length*width*width);
5) Performing statistical analysis of the size of tumors.

Figures 6A, 6B, 6C, 6D, 6E:
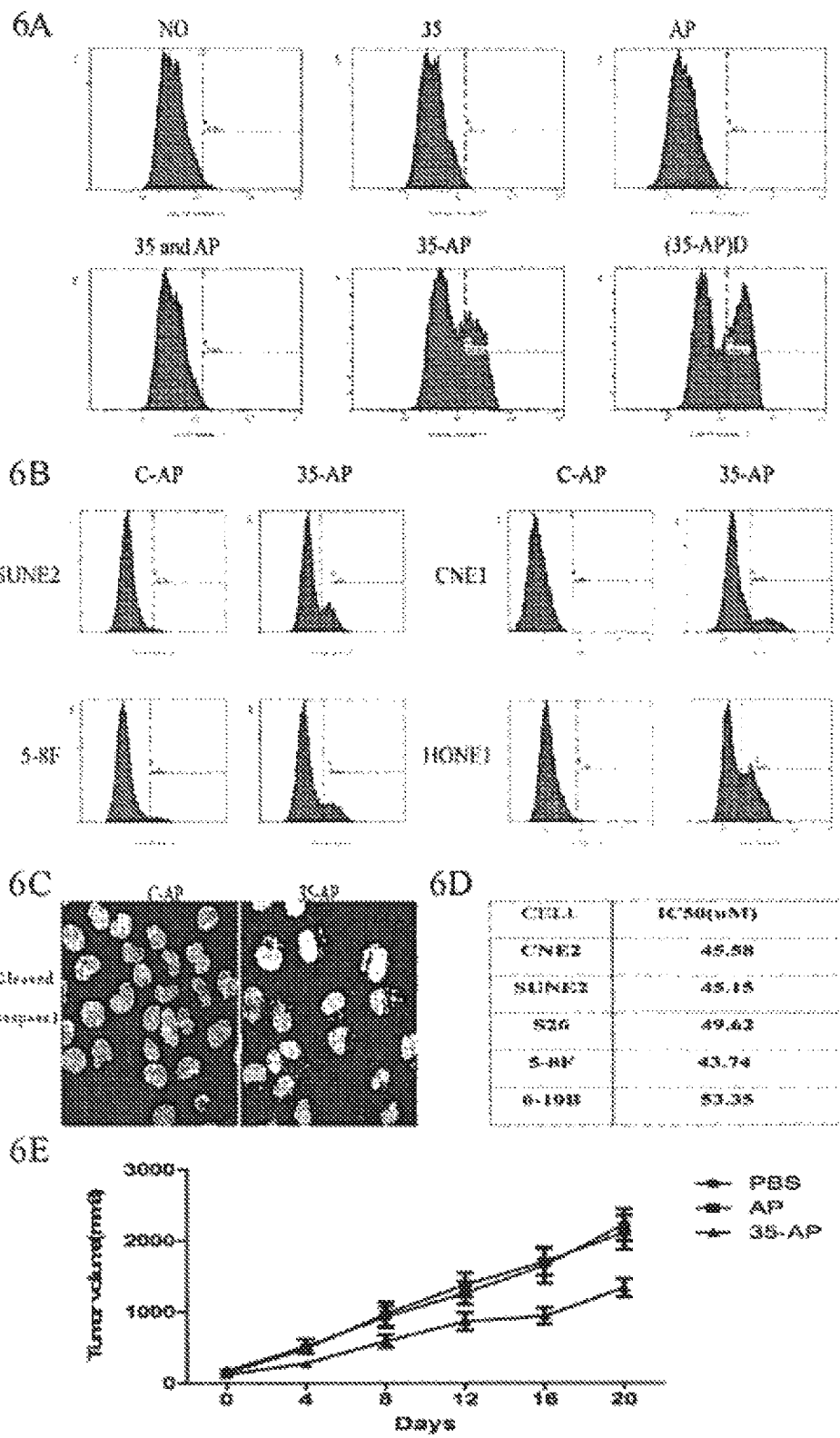
FIGS. 6A-6E show treatment results of tumor-targeting peptide coupled with apoptotic peptide.

As shown by flow cytometry analysis in FIG. 5, 35 peptide and AP peptide respectively cannot induce the apoptosis in CNE2 and their mixture cannot induce the apoptosis in CNE2 either, but 35-AP peptide can significantly promote the apoptosis compared to C-AP peptide. Meanwhile, 35-AP peptide composed by D type of amino acid also activated the apoptosis of CNE2 (FIG. 6A). 35-AP peptide incubated with other nasopharyngeal carcinoma cell lines, such as SUNE1, CNE1, 5-8F and HONE1, also led to cell apoptosis (FIG. 6B). When 35-AP peptide incubated with CNE2, cleaved Caspase3 was activated according to the cellular immunofluorescence assay (FIG. 6C). The IC50 of 35-AP peptide in various tumor cells was about 50 µM (FIG. 6D). 35-AP peptide reduced the tumor volume markedly in tumor-bearing mice compared with two control groups (FIG. 6E). All above results demonstrate that 35 peptide is applicable for the targeted treatment of NPC.

Targeted Therapy of Anti-Tumor Nanoparticles:

Coupling 35 peptide with nanoparticles containing platinum to form an anti-tumor nanoparticle derived drug and apply it to tumor targeting therapy. Detailed steps were as followed:
1) Coupled peptide or 35 peptide was mixed with PEG3.4K-PCL7.5K at the ratio of 1:1 and then equal proportion of platinum was added to form anti-tumor nanoparticles derived drug;
2) Detecting the nanoparticles under electron microscope and the release of platinum.

To observe absorption of anti-tumor nanoparticles derived drug, manipulation was as follows:
1) Incubating anti-tumor peptide-coupled nanoparticles derived drug with tumor cells at 37° C. for 4 hours;
2) Trypsinizing cells and re-suspending cells with RPMI 1640;
3) Detecting the absorption of anti-tumor nanoparticles derived drug using flow cytometry analysis.

To further detect the enrichment of anti-tumor peptide-coupled nanoparticles derived drug in tumor tissues, manipulation was as follows:
1) Intravenously injecting fluorescence nanoparticles at a ratio of 1 mg/kg weight;
2) Near-infrared imaging of tumor and organs was conducted after 6 hours.

To observe the therapeutic effect of anti-tumor peptide-coupled nanoparticles derived drug, manipulation was as followed:
1) Intravenously injecting peptide-coupled nanoparticle derived drug at 2 mg/kg weight three times every week, and continuously injecting for three weeks;
2) Dynamically monitoring the volume of tumor;
3) Obtaining the tumor and measuring the size of tumor after 3 weeks.

Figure 7A:
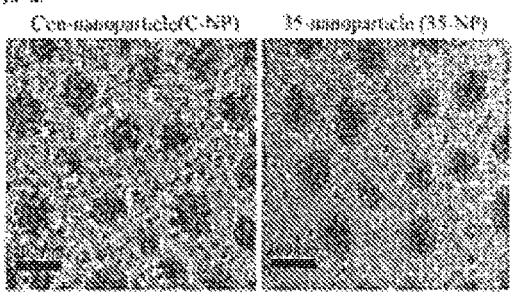
FIGS. 7A-7F show treatment result of tumor-targeting peptide coupled with nanoparticles.
Figure 7B:
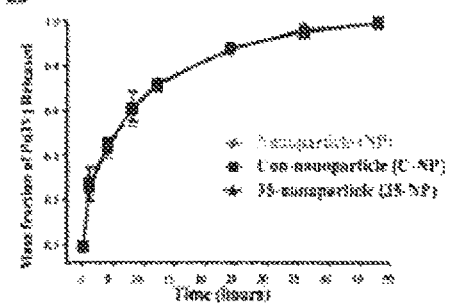
Figure 7C:
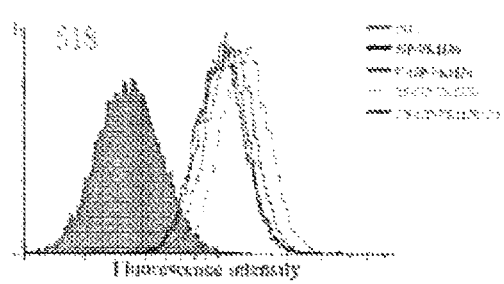
Figure 7D:
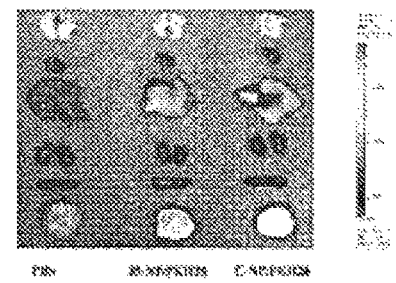
Figure 7E:
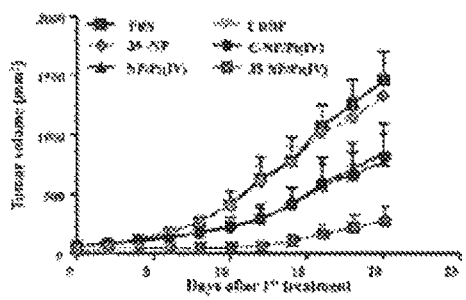
Figure 7F:
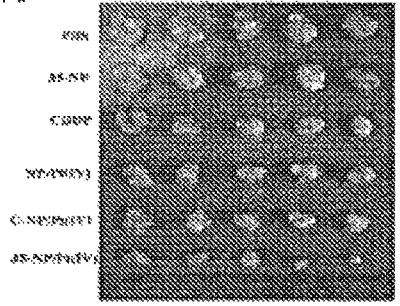

As shown in FIG. 7, the diameter of peptide-coupled nanoparticle derived drug is about 100 nm (FIG. 7A). The peptide-coupled nanoparticle derived drug can release platinum (FIG. 7B). The peptide-coupled nanoparticle derived drug is enriched in not only tumor cells in vitro (FIG. 7C) but also tumor tissues in vivo (FIG. 7D). Meanwhile, the peptide-coupled nanoparticle derived drug inhibited the growth of tumor (FIGS. 7E and 7F). All above results demonstrate the peptide-coupled nanoparticle derived drug is applicable for the targeting therapy of tumor.

The invention claimed is:

1. A tumor-targeting peptide, comprising a motif having a general formula of: RWYDENA (SEQ ID NO:8),
   wherein, a C-terminal, an N-terminal, or both the C and N terminals of the motif are selectively connected to 1-3 amino acids.

2. The tumor-targeting peptide according to claim 1, wherein the tumor-Targeting peptide is cyclized by the terminal amino acids.

3. The tumor-targeting peptide according to claim 1, wherein two ends of the peptide may be connected with one Cys, respectively.

4. A pharmaceutical composition comprising:
   a tumor-targeting peptide according to claim 1 coupled with an anti-tumor drug.

5. The pharmaceutical composition of claim 4, wherein the anti-tumor drug is selected from a tumor-killer peptide, a small molecule chemotherapeutic drug.

6. The pharmaceutical composition according to claim 5, wherein the anti-tumor drug is platinum.

7. A method for diagnosing a tumor, the method comprising:
   diagnosing tumor cells with a tumor diagnosis reagent comprising a tumor-targeting peptide according to claim 1.

8. A method of tumor-targeting drug administration comprising:
   administering a tumor-targeting peptide according to claim 1 coupled with an anti-tumor drug to a subject in need thereof.

* * * * *